US 6,559,108 B1

(12) United States Patent
Howell et al.

(10) Patent No.: US 6,559,108 B1
(45) Date of Patent: May 6, 2003

(54) PERFLUOROPOLYETHER COMPOUNDS AS MAGNETIC MEDIA LUBRICANTS

(75) Inventors: Jon Lee Howell, Bear, DE (US); David Gareth Vaughan Jones, Wheaton, IL (US); Anthony Joseph Huffmann, Chicago, IL (US); Norm V. Gitis, Cupertino, CA (US); Charles Gao, Fremont, CA (US)

(73) Assignees: E.I. du Pont de Nemours and Company, Wilmington, DE (US); Burmah Castrol Trading, Ltd., Wiltshire (GB)

( * ) Notice: Subject to any disclaimer, the term of this patent is extended or adjusted under 35 U.S.C. 154(b) by 168 days.

(21) Appl. No.: 09/712,891

(22) Filed: Nov. 15, 2000

Related U.S. Application Data

(63) Continuation-in-part of application No. 09/056,085, filed on Apr. 7, 1998, now Pat. No. 6,184,187.

(51) Int. Cl.$^7$ ............................................. C10M 147/04
(52) U.S. Cl. ........................ 508/427; 508/588; 428/422
(58) Field of Search ................. 508/427, 588; 428/422

(56) References Cited

U.S. PATENT DOCUMENTS

| | | | |
|---|---|---|---|
| 3,083,224 A | 3/1963 | Brace et al. ................ 260/461 |
| 3,306,855 A | 2/1967 | Borecki ..................... 252/49.9 |
| 3,308,207 A | 3/1967 | Seil et al. ................... 260/953 |
| 3,308,208 A | 3/1967 | Seil et al. ................... 260/955 |
| 3,337,655 A | 8/1967 | Seil et al. ................... 260/955 |
| 3,367,868 A | 2/1968 | Skehan ...................... 252/34.7 |
| 3,412,181 A | 11/1968 | Braun ........................ 260/955 |
| 3,567,802 A | 3/1971 | Garth ......................... 260/950 |
| 3,899,366 A | 8/1975 | Tajkowski ................. 148/6.16 |
| 4,536,444 A | 8/1985 | Sumiya et al. ............. 428/340 |
| 4,877,815 A | 10/1989 | Buckmaster et al. .......... 521/85 |
| 5,069,973 A | 12/1991 | Saito et al. ................. 428/421 |
| 5,091,249 A | 2/1992 | Nishikawa .................. 428/336 |
| 5,112,662 A | 5/1992 | Ng ............................. 428/64 |
| 5,128,216 A | 7/1992 | Ng ............................. 428/695 |
| 5,132,446 A | 7/1992 | Tohzuka et al. ............ 558/186 |
| 5,376,289 A | 12/1994 | Montagna et al. ......... 252/46.7 |
| 5,442,084 A | 8/1995 | Lal ............................. 558/141 |
| 5,550,277 A | 8/1996 | Paciorek et al. ............ 558/194 |
| 5,556,707 A | 9/1996 | Usuki et al. ................ 428/421 |
| 5,607,782 A | 3/1997 | Ishida et al. ............. 428/694 T |
| 5,707,742 A | 1/1998 | Usuki et al. |
| 5,874,169 A | 2/1999 | Falcone ...................... 428/421 |
| 6,083,600 A | 7/2000 | Kasai et al. ............... 428/65.4 |

FOREIGN PATENT DOCUMENTS

| | | |
|---|---|---|
| EP | 0 338 531 | 10/1989 |
| EP | 0 605 403 A2 | 7/1994 |
| EP | 0606640 A | 7/1994 |
| JP | 59154647 A | 9/1984 |
| JP | 07062377 A | 3/1995 |
| JP | 07065353 A | 3/1995 |
| JP | 07097586 A | 4/1995 |
| JP | 07192253 A | 7/1995 |
| JP | 07244893 A | 9/1995 |
| JP | 08045066 A | 2/1996 |
| SU | 255269 | 3/1970 |
| SU | 1810382 A1 | 4/1993 |

OTHER PUBLICATIONS

Yagupol'skii et al: Arylbis(heptafluoropropyl)phosphate oxides—electronic nature of the $P(O)(C_3F_7)$ grgroup; J. Gen. Chem. USSR; vol. 54. No. 2; Feb., 1984.

Pavlenko et al: Esters of bis(perfluoroalkyl)phossphinic acids; J. Gen. Chem. USSR; vol. 59. No. 3; Mar., 1989.

*Primary Examiner*—Cephia D. Toomer

(57) ABSTRACT

A recording medium comprising a phosphorus-containing fluorocarbon compound is provided. The phosphorus-containing fluorocarbon compound can be used as lubricant or as an additive to a lubricant. The phosphorus-containing fluorocarbon compound can be an esterified aryl phosphorus compound, a salt thereof, or combinations thereof.

19 Claims, No Drawings

PERFLUOROPOLYETHER COMPOUNDS AS MAGNETIC MEDIA LUBRICANTS

This application is a continuation-in-part of U.S. patent application Ser. No. 09/056,085, filed Apr. 7, 1998, now, U.S. Pat. No. 6,184,187.

FIELD OF INVENTION

This invention relates to a recording medium comprising a phosphorus-containing fluorocarbon compound as lubricant.

BACKGROUND OF THE INVENTION

Magnetic disk drives, magnetic hard disks or magnetic optical disks, are devices well known to one skilled in the art for storing information. The devices can use a rotatable thin film magnetic media with data tracks, a read/write transducer for reading/writing the information on the tracks, a slider for holding the transducer to the tracks, and a flying mode above the media. Ideally, the slider can fly as close as possible to the media leaving small spacing to allow the transducer to distinguish between the magnetic field from the closely spaced regions on the disk. During operation, the transducer head slides against the surface of the disk as the disk begins to rotate. The transducer head, when the disk reaches a predetermined rotational speed, floats in air at a predetermined distance from the surface of the disk. When the operation of the disk drive terminates, the transducer head begins to slide against the surface. Such sliding repeats every time the head and disk assembly is driven.

To maintain the slider as close as possible to the media or the transducer head as close to its recording surface as possible to minimize the flying height of the head, it requires a smooth recording surface. However, excessive stiction (static coefficient of friction) and friction can result if the head surface and the recording surface are too flat. Excessive stiction and friction can cause wear to the head and recording surfaces.

A phosphorus-containing high molecular weight perfluoroalkylpolyether compound has been used as a disk drive lubricant as disclosed in U.S. Pat. No. 5,874,169.

There is a continuing need to lubricate or coat the thin film disks and sliders to ensure the regular transducer fly height. There is also a need to develop a lubricant or coating that is stable at the operating conditions of the disks as well as during the manufacture of magnetic recording media.

SUMMARY OF THE INVENTION

The invention provides a recording medium comprising a phosphorus-containing fluorocarbon compound. The phosphorus-containing fluorocarbon compound can be an esterified phosphorus compound, a salt thereof, or combinations thereof.

DETAILED DESCRIPTION OF THE INVENTION

Generally, a recording medium includes a magnetic medium (hard or flexible), magneto-optical medium, optical medium, or combinations thereof and can include either audio or video tape. A magnetic recording medium can comprise a magnetic layer on a non-magnetic substrate. The magnetic layer can comprise a protective overcoat on the magnetic layer. A lubricant can be present as a lubricant topcoat on the magnetic layer or on the protective overcoat, if present. The lubricant or lubricant topcoat comprises, consists essentially of, or consists of the phosphorus-containing fluorocarbon compound. The non-magnetic substrate, the magnetic layer, and the protective overcoat are well known to one skilled in the art. See, for example, U.S. Pat. No. 5,874,169, disclosure of which is incorporated herein by reference. Therefore the description of the non-magnetic substrate, the magnetic layer, and the protective overcoat is omitted herein for the interest of brevity. The invention disclosed herein is suitable for all recording media.

According to the invention, a magnetic recording medium comprising a phosphorus-containing fluorocarbon compound is provided. The phosphorus-containing fluorocarbon compound can be used as lubricant or as an additive to a lubricant. The phosphorus-containing fluorocarbon compound can be an esterified aryl phosphorus compound, a salt thereof, or combinations thereof.

The esterified aryl phosphorus compound can be a perfluoropolyether- or perfluoroalkyl-containing and phosphorus-containing aryl compound selected from the group consisting of Classes A, B, and C, and combinations of two or more thereof.

The Class A compound can be a perfluoropolyether- or perfluoroalkyl-containing and phosphorus-containing compound selected from the group consisting of partially esterified aryl phosphates, partially esterified aryl phosphonates, and salts thereof, containing either (i) a mono-alkylene oxide or poly-alkylene oxide or phenylene oxide linking group between the phosphorus and a fluorocarbon group, or (ii) no linking group between the phosphorus and fluorocarbon group, and (iii) combinations of (i) and (ii). Representative compounds within Class A are shown below.

Class A(i) compounds having a mono- or poly-alkylene oxide linking group include those having formulae I, II, III, or combinations of two or more thereof.

[Rf—Y—]$_{(2-x)}$—P(E)—[O$_b$C$_6$R$_5$][OM]$_x$ (Formula I)

[Rf'—Y—]$_{(2-x)}$—P(E)—[O$_b$C$_6$R$_5$][OM]$_x$ (Formula II)

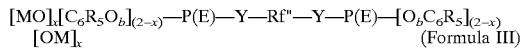
[MO]$_x$[C$_6$R$_5$O$_b$]$_{(2-x)}$—P(E)—Y—Rf"—Y—P(E)—[O$_b$C$_6$R$_5$]$_{(2-x)}$[OM]$_x$ (Formula III)

where:

Y is (CH$_2$)$_z$O(CH$_2$CH$_2$O)$_{z'}$, wherein z is 1 to 4 and z' is 0, 1 or 2, or Y is C$_6$R$_4$, x is 0.05 to 1, E is oxygen or sulfur, b is 0 or 1, R is the same or different substituent chosen from hydrogen, halogen, alkyl, aryl, nitro, cyano, alkoxy, primary and secondary amino, sulfonyl, carboxyl, or phenoxy, and M is hydrogen, alkali metal, alkaline earth metal, or ammonium.

Rf is a polyether chain having a molecular weight ranging from 400 to 15,000 and composed of repeating units selected from the group consisting of:

J—O—(CF(CF$_3$)CF$_2$O)$_c$—(CFXO)$_d$—CFZ where:

J is a fluoroalkyl group selected from the group consisting of CF$_3$, C$_2$F$_5$, C$_3$F$_7$, CF$_2$Cl, C$_2$F$_4$Cl, and C$_3$F$_6$Cl, X is —F or —CF$_3$, Z is —F, —Cl or —CF$_3$, and c and d are numbers such that the c/d ratio ranges from 0.01 to 0.5, and the molecular weight ranges from 400 to 15,000;

$J^1$—O—$(CF_2CF_2O)_e$—$(CF_2O)_f$—$CFZ^1$ where:
$J^1$ is a fluoroalkyl group selected from the group consisting of $CF_3$, $C_2F_5$, $CF_2Cl$, and $C_2F_4Cl$,
$Z^1$ is —F or —Cl, and
e and f are numbers such that the e/f ratio ranges from 0.5 to 2 and, the molecular weight ranges from 400 to 15,000;
$J^2$—O—$(CF(CF_3)CF_2O)_j$—$CF(CF_3)$ where:
$J^2$ is $C_2F_5$ or $C_3F_7$, and
j is a number such that the molecular weight ranges from 400 to 15,000;
$J^3$—O—$(CQZ^2$—$CF_2CF_2$—O$)_k$—$CQZ^2$—$CF_2$ where:
$J^3$ is selected from the group consisting of $CF_3$, $C_2F_5$, and $C_3F_7$,
Q and $Z^2$, equal or different, are F, Cl or H, and
k is a number such that the molecular weight ranges from 400 to 15,000;
$J^4$—O—$(CF_2CF_2O)_l$—$CF_2$ where:
$J^4$ is $CF_3$, or $C_2F_5$ and
l is a number such that the molecular weight ranges from 400 to 15,000;
$J^5$—$(CF(CF_3)CF_2O)_g$—$(CF_2CF_2O)_h$—$(CFX$—O$)_i$—CFZ— where:
X and Z are as defined above, and
g, h and i are numbers such that (g+h) ranges from 1 to 50, the i/(g+h) ratio ranges from 0.1 to 0.05, and the molecular weight is from 400 to 15,000;
Rf' is $Z^2$—$(CF_2)_m$ where:
$Z^2$ is H, F, or Cl, and
m has a value from 2 to 20; and
Rf" is a perfluoropolyether chain having a number average molecular weight of 500 to 15,000, selected from the group consisting of:
(i) $(CF_2CF_2O)_n$—$(CF_2O)_o$—$CF_2$
wherein the units with formulae $C_2F_4O$ and $CF_2O$ are randomly distributed along the chain, and n and o are integers, whose ratio, n/o, is in the range of from 0.3 to 5;
(ii) $(C_3F_6O)_p$—$(CF_2CF_2O)_q$—$(CFXO)_r$—$CF_2$ wherein
X is F or $CF_3$ and
p, q and r are numbers such that (p+q) ranges from 1 to 50, and the r/(p+q) ratio ranges from 0.1 to 0.05, and the molecular weight is from 400 to 15,000;
(iii) $((CQZ^2)CF_2CF_2O)_s$—$CF_2$—$CF_2$ where
Q and $Z^2$, equal or different, are F, Cl or H, and s is a number such that the molecular weight ranges from 400 to 15,000; and
(iv) $(CF_2O)$—$(CF_2CF_2O)_t$—$CF_2$ where t is a number such that the molecular weight ranges from 400 to 15,000.

Representative compounds within Class A(i) include:

For Formula I: $F(CF(CF_3)CF_2O)_nCF(CF_3)CH_2OP(O)[OH]C_6H_5$ and
$F(CF(CF_3)CF_2O)_nCF(CF_3)CH_2OP(O)[OH]OC_6H_5$
where n is 4 to 10.

For Formula II: $F(CF_2)_mCH_2CH_2OP(O)[OH]C_6H_5$ and $F(CF_2)_mCH_2CH_2OP(O)[OH]OC_6H_5$ where m is 4, 6 or 8.

For Formula III: $[HO](C_6H_5)P(O)OCH_2$—$(CF_2CF_2O)_n$—$(CF_2O)_o$—$CF_2$—$CH_2OP(O)(C_6H_5)[OH]$ and $[HO](H_5C_6O)P(O)OCH_2$—$(CF_2CF_2O)_n$—$(CF_2O)_o$—$CF_2$—$CH_2OP(O)(OC_6H_5)[OH]$ where (n+o)=8 and n/o=1.

Class A(ii) compounds having no mono or poly alkylene or phenylene oxide linking group include those having formulae IV, V, VI, and combinations of two or more thereof.

[Rf—]$_{(2-x)}$—P(E)—[O$_b$—$C_6R_5$][OM]$_x$ (Formula IV)

[Rf'—]$_{(2-x)}$—P(E)—[O$_b$C$_6$R$_5$][OM]$_x$ (Formula V)

[MO]$_x$[C$_6$R$_5$O$_b$]$_{(2-x)}$—P(E)—Rf"—P(E)—[O$_b$C$_6$R$_5$]$_{(2-x)}$[OM]$_x$ (Formula VI)

wherein Rf, Rf', Rf", x, E, b, R, and M are as previously defined for Formulae I to III.

Representative compounds within Class A(ii) include:
For Formula IV: $F(CF(CF_3)CF_2O)_nCF(CF_3)P(O)[OH]C_6H_5$ and $F(CF(CF_3)CF_2O)_nCF(CF_3)P(O)[OH]OC_6H_5$ where n is 4 to 10.

For Formula V: $F(CF_2)_mP(O)[OH]C_6H_5$ and $F(CF_2)_mP(O)[OH]OC_6H_5$ where m is 4, 6 or 8.

For Formula VI: $[HO](C_6H_5)P(O)$—$(CF_2CF_2O)_n$—$(CF_2O)_o$—$CF_2$—$P(O)(C_6H_5)[OH]$ and $[HO](H_5C_6O)P(O)$—$(CF_2CF_2O)_n$—$(CF_2O)_o$—$CF_2$—$P(O)(OC_6H_5)[OH]$ where (n+o) is 8, and n/o is 1.

The Class B compound can be an asymmetrical perfluoropolyether- or perfluoroalkyl-containing and phosphorus-containing compound being either (i) aryl phosphites or aryl phosphates containing a mono-alkylene oxide or poly-alkylene oxide or phenylene oxide linking group between the phosphorus and a perfluoroether group, or (ii) aryl phosphines, aryl phosphinites, aryl phosphonites, aryl phosphine oxides, aryl phosphinates or aryl phosphonates with no linking group between the phosphorus and a fluorocarbon group, or (iii) combinations of (i) and (ii). Representative compounds within Class B have the following formulae.

Class B(i) compounds having a mono- or poly-alkylene oxide linking group include formulae VII, VIII, or combinations thereof.

[Rf—Y—]$_{(3-y)}$—P(E)$_a$—[O—C$_6$R$_5$]$_y$ (Formula VII)

(C$_6$R$_5$O)$_2$—P(E)$_a$—Y—Rf"—Y—P(E)$_a$—(OC$_6$R$_5$)$_2$ (Formula VIII)

wherein R, Rf, Y, and E are as previously defined and y is 0.05 to 2, and a is 0 or 1.

Class B(ii) compounds having no polyalkylene oxide linking group include those having the formulae Ix, X, IX, or combinations of two or more thereof.

[Rf]$_{(3-y)}$—P(E)$_a$—[O$_b$C$_6$R$_5$]$_y$ (Formula IX)

[Rf']$_{(3-y)}$—P(E)$_a$—[O$_b$C$_6$R$_5$]$_y$ (Formula X)

[C$_6$R$_5$O]$_2$—P(E)$_a$—Rf"—P(E)$_a$—[O$_b$C$_6$R$_5$]$_2$ (Formula XI)

wherein Rf, Rf', Rf", a, b, E, R, y, and n are as previously defined for Formulae I to VIII.

Representative compounds within Class B(i) include:
For Formula VII: $[F(CF(CF_3)CF_2O)_nCF(CF_3)CH_2O]P(OC_6H_5)_2$ and $[F(CF(CF_3)CF_2O)_nCF(CF_3)CH_2O]_2P(O)(OC_6H_5)$ where n is 4 to 10.

For Formula VIII: $(H_5C_6O)_2P$—$(CF_2CF_2O)_n$—$(CF_2O)_o$—$CF_2$—$P(OC_6H_5)_2$ and $(H_5C_6O)P(O)$—$(CF_2CF_2O)_n$—$(CF_2O)_o$—$CF_2$—$P(O)(OC_6H_5)_2$ where n is (n+o) is 8, and n/o is 1.

Representative compounds within Class B(ii) include:
For Formula IX: $F(CF(CF_3)CF_2O)_nCF(CF_3)P(C_6H_5)_2$, $[F(CF(CF_3)CF_2O)_nCF(CF_3)]_2P(OC_6H_5)$, $[F(CF(CF_3)CF_2O)_nCF(CF_3)]P(O)(C_6H_5)_2$, and $[F(CF(CF_3)CF_2O)_nCF(CF_3)]_2P(O)(OC_6H_5)$ where n is 4 to 10.

For Formula X: $F(CF_2)_mP(C_6H_5)_2$, $[F(CF_2)_m]_2P(OC_6H_5)$, $F(CF_2)_mP(OC_6H_5)_2$, $[F(CF_2)_m]P(O)(C_6H_5)_2$, $[F(CF_2)_m]_2P(O)(OC_6H_5)$, and $F(CF_2)_mP(O)(OC_6H_5)_2$ where m is 4, 6, or 8.

For Formula XI: $(H_5C_6)_2P—(CF_2CF_2O)_n—(CF_2O)_o—CF_2—P(C_6H_5)_2$, $(H_5C_6O)_2P—(CF_2CF_2O)_n—(CF_2O)_o—CF_2—P(OC_6H_5)_2$, $(H_5C_6)_2P(O)—(CF_2CF_2O)_n—(CF_2O)_o—CF_2—P(O)(C_6H_5)_2$, and $(H_5C_6O)_2P(O)—(CF_2CF_2O)_n—(CF_2O)_o—CF_2—P(O)(OC_6H_5)_2$ where (n+o) is 8; and n/o is 1.

Class C compound can be a perfluoropolyether- or perfluoroalkyl-containing and phosphorus-containing compound selected from the group consisting of partially esterified phosphates, phosphonates, and salts thereof, containing either (i) a mono- or poly-alkylene oxide or phenylene oxide linking group between the phosphorus and a fluorocarbon group, or (ii) no linking group between the phosphorus and fluorocarbon group.

Representative compounds within Class C include compounds having the formulae XII to XIV shown below.

   (Formula XII)

   (Formula XIII)

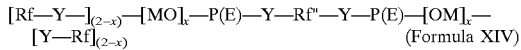   (Formula XIV)

where Y, x, R, Rf, Rf', Rf", M and E are the same as described above.

Representative compounds within Class C(i) include:

For Formula XII: $F(CF(CF_3)CF_2O)_nCF(CF_3)CH_2OP(O)[OH]_2$ and $[F(CF(CF_3)CF_2O)_nCF(CF_3)CH_2O]_2P(O)[OH]$ where n is 4 to 10.

For Formula XIII: $F(CF_2)_mCH_2CH_2OP(O)[OH]_2$ and $[F(CF_2)_mCH_2CH_2O]_2P(O)[OH]$ where m is 4, 6 or 8.

For Formula XIV: $[HO]_2P(O)OCH_2—(CF_2CF_2O)_n—(CF_2O)_o—CF_2—CH_2OP(O)[OH]_2$ and

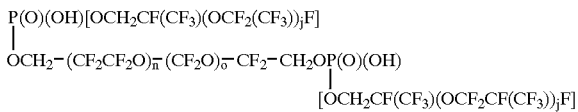

where (n+o)=8 and n/o=1 and j=4 to 10.

Class C(ii) compounds do not have a mono- or poly-alkylene oxide or phenylene linking group and can be represented by formulae XV to XVII shown below.

   (Formula XV)

   (Formula XVI)

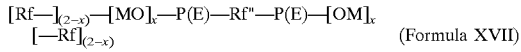   (Formula XVII)

wherein Rf, Rf', Rf", x, E, and M are as previously defined.

Representative compounds within Class C(ii) include:

For Formula XV: $F(CF(CF_3)CF_2O)_nCF(CF_3)P(O)[OH]_2$ and $[F(CF(CF_3)CF_2O)_nCF(CF_3)]_2P(O)[OH]$ where n is 4 to 10.

For Formula XVI: $F(CF_2)_mP(O)[OH]_2$ and $[F(CF_2)_m]_2P(O)[OH]$ where m is 4, 6 or 8.

For Formula XVII: $[HO]_2P(O)—CF_2O—(CF_2CF_2O)_n—(CF_2O)_o—CF_2—P(O)[OH]_2$ and

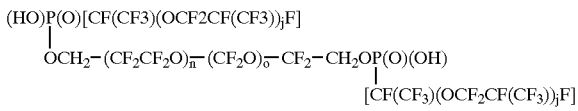

where (n+o) is 8, and n/o is 1 and j=4 to 10.

The above-disclosed compounds can be produced by any methods known to one skilled in the art. The following disclosure shows some examples for synthesizing these compounds.

For compounds of Classes A(i) and B(i), the syntheses of can be accomplished by the method described by Moreton in U.S. Pat. No. 2,694,083, disclosure of which is incorporated herein by reference. Briefly, the synthesis can be carried out by reaction of either (a) aryloxy substituted or aryl substituted phosphorus oxychlorides at elevated temperatures with a fluoroalcohol of the formula Rf—OH, or (b) with the corresponding fluoroalkyl phosphorus dichloride and a substituted phenol in which Rf is the same as that disclosed above. Alternately, the compounds can be produced by mixing the reactants in the presence of a dry aprotic organic base such as triethylamine or pyridine, and allowing the reaction to proceed at room temperature until complete either with or without solvent as described by Paciorek in U.S. Pat. No. 5,550,277. Control over the specific reaction products is by stoichiometry. This reaction is followed by hydrolysis to form the corresponding acid ester. Additionally, the products are neutralized with a solution or suspension of the hydroxide or carbonate of the alkali metal or alkaline earth metal, or ammonium hydroxide solution, prior to isolation to provide the corresponding salt, producing a rust and corrosion prevention additive compatible with perfluoropolyether oils and greases containing sodium nitrite. The solution is washed with water to remove excess acid and salts or base and salts, then vacuum stripped to remove solvents and volatiles.

Compounds of Classes A(ii) and B(ii) can be produced by contacting a perfluoroalkyl or perfluoroether iodide with elemental phosphorus at an elevated temperature to produce a diiodophosphine, which can then be contacted with either a metalated aryl or aryloxy compound to produce the corresponding phosphorus(III) compounds; or oxidized with chlorine/water or hydrogen peroxide to produce the phosphorus(V) oxide. The phosphorus(III) can be oxidized with chlorine followed by treatment with $H_2S$ or $Na_2S$ to produce the thiophosphorus(V) materials.

Because each of the above-disclosed reactions is well known to one skilled in the art, the descriptions are omitted herein.

The phosphorus-containing fluorocarbon compound preferably has a molecular weight of between about 500 and about 100,000, more preferably between 1,000 and 6,000.

The viscosity of the phosphorus-containing fluorocarbon compound is preferably sufficient to minimise capillary action of the lubricant between the surface of the substrate and the disk head. The viscosity of the phosphorus-containing fluorocarbon compound is preferably between about 1 and 1000 cP (0.001 and 1 Pa.s) in the temperature range of about 0° C. to about 85° C.

The phosphorus-containing fluorocarbon compound can also be used as an additive for the recording medium. The phosphorus-containing fluorocarbon compound can be diluted in a solvent before it is applied to the disk. Any solvent having a vapour pressure that can readily evaporates at ambient temperature and pressure can be used. Examples of such solvent can include a commercially available fluorocarbon, hydrofluorocarbon, perfluorocarbon, or combinations of two or more thereof The concentration of the phosphorus-containing fluorocarbon compound in the solvent, if used, can be from about 0.0001 to about 99% by weight An impurity, if present, is preferably removed from the phosphorus-containing fluorocarbon compound before the phosphorus-containing fluorocarbon compound is applied to the recording medium. The removal, if required, can be carried out by, for example, ultrafiltration with a filter of, for example, 0.2 µm. During filtration, the phosphorus-containing fluorocarbon compound can be dissolved in a solvent. Following filtration, the solvent can be removed by any means known to one skilled in the art such as, for example, evaporation, and can be recycled/re-used.

The phosphorus-containing fluorocarbon compound can be applied to the magnetic recording medium by any means known to one skilled in the art such as, for example, dip coating, spraying, spin coating or vapor deposition. The pulling-up speed, the density of the phosphorus-containing fluorocarbon compound and the surface tension are relevant for determining the film thickness of the phosphorus-containing fluorocarbon compound. See 'Dip-Coating of Ultra-Thin Liquid Lubricant and its Control for Thin-Film Magnetic Hard Disks' in IEEE Transactions on Magnetics, vol. 31, no. 6, November 1995, for further details.

The lubricant can be applied to a thickness of less than about 300 nm, and most preferably a thickness of about 100 nm to about 300 nm.

Bonding of the lubricant to the magnetic recording medium can be improved by removing impurities from the surface of the recording medium. Impurities can be removed from the surface of the recording medium using a mild oxygen plasma or an isopropanol vapor rinse. However, less cleaning of the surface of the recording medium is required when using the lubricant of the present invention.

The following examples further illustrate the invention and should not be construed as to unduly limit the scope of the invention.

EXAMPLES

The lubricant was applied to the magnetic recording medium by standard methods such as dip coating, spraying, spin coating or vapor deposition. The pulling-up speed, the density of the lubricant and the surface tension are relevant for determining the film thickness of the lubricant. Such standard methods are described in "Dip-Coating of Ultra-Thin Liquid Lubricant and its Control for Thin-Film Magnetic Hard Disks" in IEEE Transactions on Magnetics, Vol. 31, No. 6, November 1995. The lubricant was applied to a thickness of less than 300 nm. The lubricant is preferably applied to a thickness of about 100–300 nm. In each example, the lubricants were applied to standard magnetic medium which were 95-mm nickel-phosphorus (NiP, about 10 um thick) plated aluminum substrates with magnetic coatings, on top of which was diamond-like-carbon (DLC) film aluminum hard disks by a standard dip-coating method using a gravity disc lubricating machine, used according to the manufacture's instructions. The disks, oriented vertically, were submerged into a tank containing the lubricant solution and then pulled vertically out of the lubricant solution at a steady speed of 1 mm/s. The solvent was evaporated using standard techniques leaving a thin layer of lubricant on the disks.

Thickness measurements were made using a FTIR from Nicolet, Model Magnet-560, XPS (ESCA) was from Physical Electronics and GC/MS from Hewlett Packard as described in Application of Pattern Recognition FTIR Methodology to The Study of Additive/Lubricant Interactions at the Molecular Level, Tribology of Information Storage, December 1999, TISD, Santa Clara, by C. Gao, B. Liu and K. Johnson.

The lubricated discs were subjected to the following measurements
1. contact angle;
2. contact start stop with park stiction;
3. spin-off test; and
4. fly-stiction test.

Measurements are shown in the following Tables.

Example 1

A perfluoroether or perfluoroalkyl and phosphorus-containing compound of Class C(i) was prepared as described by Howell in Patent WO 99/51612 from phosphoryl chloride and $Rf'''(OC_3F_6)_c(OCF_2)_dOCF_2CH_2OH$ where $Rf'''$ is $CF_3$, $C_2F_5$, $CF_2Cl$, or $C_2F_4Cl$ and a molecular weight of 500 to 1500, which was dissolved to a ratio of 0.01% w/w in HFE-7100®, a hydrofluoroether solvent sold by 3M, Minneapolis, Minn. and applied as described above.

Example 2

MICROCOTE® 2000, available from Castrol North America Inc., (Chicago Ill., a perfluoroether or perfluoroalkyl and phosphorus-containing compound of Class A(i) as described by Howell in Patent WO 99/51612) was dissolved to a ratio of 0.01% w/w in a hydrofluoroether solvent, 3M HFE-7100® and applied as described above.

Comparative Example 1

Fomblin Z-Dol® 2000 (available from Montefluos SpA/ Ausimont, Italy) is a perfluoropolyether having two hydroxyl end groups. It was also dissolved in the hydrofluoroether solvent, and applied according to the procedure of Example 1.

Comparative Example 2

A solution of Fomblin Z-Dol® 2000 (0.08%) and X1P® (0.003%, a phosphazene-containing disk lubricant available from Dow Chemical Co, Midland Mich.) was made in HFE-7100® solvent and applied according to the procedure of Example 1.

Test 1. Contact Angle:
Contact angles were measured conventionally and the results are shown in

TABLE 1

Contact Angle Measurements

| Lubricant Thickness, Å (nm) | Position on Disk | Example 1 (°) | Example 2 (°) | Comparative Example 1 (°) |
|---|---|---|---|---|
| 15 (150) | 0° | 49 | 55 | 64 |
|  | 90° | 49 | 55 | 65 |
|  | 180° | 49 | 55 | 65 |
|  | 270° | 49 | 55 | 65 |
|  | Average | 49 | 55 | 65 |
| 20 (200) | 0° | 46 | 50 | 69 |
|  | 90° | 46 | 50 | 68 |
|  | 180° | 46 | 49 | 70 |
|  | 270° | 45 | 50 | 69 |
|  | Average | 46 | 50 | 69 |
| 25 (250) | 0° | 42 | 46 | 72 |
|  | 90° | 42 | 45 | 72 |
|  | 180° | 42 | 45 | 73 |
|  | 270° | 42 | 45 | 72 |
|  | Average | 42 | 45 | 72 |

The results in Table 1 show that the lubricant of the present invention exhibits lower contact angles than the comparative lubricant, FOMBLIN Z-DOL. Lubricants with lower contact angles or better wetting bond more strongly to the disk surface.

Test 2. Contact Start Stop with Park Stiction:

This test is a standard test that is used to study the durability and stiction levels of disks at various environmental conditions such as ambient, hot/wet and cold/dry.

The procedure was carried out as follows:

10,000 Contact Start Stop (CSS) cycles at ambient (25° C., 30% RH);

10,000 CSS cycles at hot/wet (55° C., 85% RH); and 10,000 CSS cycles at cold/dry (10° C., 10% RH).

The samples were tested using six common heads (50% tri-pad head sliders), per common head sequence: 3 sec acceleration from 0 to 7,200 rpm; 3 sec flying over the landing zone at 7,200 rpm; 3 sec deceleration from 7,200 rpm to 0; and 3 sec rest on the disk landing zone. At the end of each test there was a 12-hour rest (park), followed by breakaway stiction measurements. The six heads were photographed before and after the test. The stiction results are shown in Table 2.

As shown in Table 2, at a thickness of 15 Å (150 nm), only disks covered in the lubricants of the invention survived the test. The disks covered in the comparative lubricant showed severe wear.

At thicknesses of both 20 and 25 Å (200 and 250 nm), the lubricants of the invention exhibited less start up stiction that the comparative lubricant.

The lubricants of the invention exhibited their best performance over the comparative lubricant under the hot/wet and cold/dry conditions.

Example 2 exhibited an optimal thickness below that of the comparative example.

These results show that the lubricants in accordance with the invention exhibit better stiction and durability performance when compared to the comparative lubricant.

Test 3. Spin-Off Test

This test is used by disk manufacturers and includes spinning disks at high speed and elevated temperature or delubing the disks with HFE-7100® from 3M to monitor the lubricant mobility on the disk surface.

The disks were spun at 10,000 rpm for 5 days continuously at 50° C., 30% Relative humidity (RH, no contact with

TABLE 2

CSS and Stiction results

| Lubricant Thickness Å (nm) | Environmental Conditions | No. of Cycles | Example 1 (g) | Example 2 (g) | Comparative Ex. 1 (g) | Comparative Ex. 2 (g) |
|---|---|---|---|---|---|---|
| 15 (150) | Ambient | 10,000 | 4.25 | 4.82 | Wear | Wear |
| | Hot/wet | 10,000 | 5.76 | 10.64 | Wear | Wear |
| | Cold/dry | 10,000 | 4.41 | 8.72 | Wear | Wear |
| | Ambient | 40,000 | 4.63 | 5.05 | n/a | n/a |
| 20 (200) | Ambient | 10,000 | 4.68 | 3.19 | 3.67 | 3.08 |
| | Hot/wet | 10,000 | 6.92 | 6.1 | 7.71 | 6.57 |
| | Cold/dry | 10,000 | 4.93 | 3.28 | 4.16 | 3.75 |
| | Ambient | 40,000 | 4.76 | 3.27 | 4.33 | 3.62 |
| 25 (250) | Ambient | 10,000 | 5.05 | 5.59 | 5.95 | 5.44 |
| | Hot/wet | 10,000 | 11.13 | 8.57 | 13.16 | 9.09 |
| | Cold/dry | 10,000 | 8.96 | 3.62 | 6.46 | 5.81 |
| | Ambient | 40,000 | 5.35 | 5.84 | 6.56 | 5.92 | n/a, failed before 10,000 cycles.

any heads). The lubricant thickness on both sides of the disks was measured before and after the test.

TABLE 3

Spin-Off Test Results

| Nominal Lubricant Thickness Å (nm) | Post-treatment | Example 1 Å (nm) [% remaining*] | Example 2 Å (nm) [% remaining*] | Comparative Example 1 Å (nm) [% remaining*] |
|---|---|---|---|---|
| 15 (150) | Lubricating | 18.4 (184) | 18.3 (183) | 17.9 (179) |
| | Tape burnishing | 15.5 (155) [84] | 15.1 (151) [83] | 14.5 (145) [81] |
| | delubing | 14.5 (145) [79] | 12.6 (126) [69] | 6.5 (65) [36] |
| | spin-off | 12.3 (123) [67] | 14.1 (141) [77] | 10 (100) [56] |
| 20 (200) | Lubricating | 22.1 (221) | 22.3 (223) | 22 (220) |
| | Tape burnishing | 19.8 (198) [90] | 19 (190) [85] | 19.1 (191) [87] |
| | delubing | 16.2 (162) [73] | 15.5 (155) [70] | 7.3 (73) [33] |
| | spin-off | 16.7 (167) [76] | 18.2 (182) [82] | 11.4 (114) [52] |
| 25 (250) | Lubricating | 27.1 (271) | 29.9 (299) | 27.7 (277) |
| | Tape burnishing | 24.9 (249) [92] | 25.1 (251) [84] | 25 (255) [90] |
| | delubing | 19.5 (195) [72] | 15.9 (159) [53] | 7.7 (77) [28] |
| | spin-off | 19 (190) [70] | 22.9 (229) [77] | 16 (160) [58] |

*% original actual lubricant thickness remaining after test, "Lubricating" thickness represents 100%.

The results in Table 3 show that the lubricants of the present invention exhibit a much lower lubricant loss than the comparative lubricant. The lubricants of the present invention exhibit reduced lubricant loss in delubing and spin-off because they bond to the surface of the disk better than the comparative lubricant (cf. Contact Angle Test Results in Table 1).

Test 4. Fly-Stiction Test:

This test involves continuously sweeping heads over the whole of the disk surfaces for a substantial period of time; parking the heads; and measuring the fly-stiction. This is an advanced technique that is widely used by all drive and disk manufacturers to characterise a head-disk interface with low-flying heads. The disks were matched with the same type of heads used in the CSS test (Test 2 above). The test was designed for head sliders to sweep across the disk surface for 3 continuous days at 55° C., 85% RH. The heads were then rested at the landing zone for 12 hours, twice. After each rest period, breakaway stiction values were measured. The results are shown below in Table 4.

TABLE 4

Fly-Stiction Test Results.

| Lubricant Thickness Å (nm) | Environmental Conditions | 24-hr Park after Fly for | Examples (g) 1 | Examples (g) 2 | Comparative Examples (g) 1 | Comparative Examples (g) 2 |
|---|---|---|---|---|---|---|
| 15 (150) | Hot/wet | 3 days | 4.51 | 6.02 | 6.75 | 5.89 |
| 15 (150) | Hot/wet | 5 days | 4.76 | 6.38 | 7.93 | 6.84 |
| 20 (200) | Hot/wet | 3 days | 5.01 | 4.71 | 10.07 | 7.2 |
| 20 (200) | Hot/wet | 5 days | 5.27 | 4.95 | 12.36 | 8.09 |
| 25 (250) | Hot/wet | 3 days | 10.49 | 9.17 | 12.54 | 10.96 |
| 25 (250) | Hot/wet | 5 days | 11.08 | 10.23 | 14.06 | 12.42 |

As shown in the Table 4, Example 1 exhibited the lowest fly stiction test result at 15 Å (150 nm). At 20 and 25 Å (200 and 250 nm), both Examples 1 and 2 exhibited better results that the Comparative Examples. The best results were seen at 20 Å (200 nm). Example 2 had the same optimal thickness as the Comparative Examples. These results show that the lubricants in accordance with the present invention exhibit better flying stiction performance than the Comparative Examples.

What is claimed is:

1. A recording medium comprising a lubricant wherein
said recording medium is magnetic medium, magneto-optical medium, or optical medium;
said lubricant comprises a phosphorus-containing fluorocarbon compound selected from the group consisting of compound A, compound B, compound C, and combinations of two or more thereof;
said compound A is a perfluoropolyether- or perfluoroalkyl-containing and phosphorus-containing compound selected from the group consisting of partially esterified aryl phosphates, partially esterified aryl phosphonates, and salts thereof, containing either (i) a mono-alkylene oxide or poly-alkylene oxide or phenylene oxide linking group between the phosphorus and a fluorocarbon group, (ii) no linking group between the phosphorus and fluorocarbon group, or (iii) combinations of (i) and (ii);
said compound B is an asymmetrical perfluoropolyether- or perfluoroalkyl-containing and phosphorus-containing compound selected from the group consisting of (i) aryl phosphites or phosphates containing a phenylene oxide linking group between the phosphorus and a perfluoroether group, (ii) aryl phosphines, aryl phosphinites, aryl phosphonites, aryl phosphine oxides, aryl phosphinates or aryl phosphonates with no linking group between the phosphorus and a fluorocarbon group, and (iii) combinations of (i) and (ii); and
said compound C is a perfluoropolyether- or perfluoroalkyl-containing and phosphorus-containing compound selected from the group consisting of partially esterified phosphates, partially esterified phosphonates, and salts thereof, containing either (i) a phenylene oxide linking group between the phosphorus and a fluorocarbon group, (ii) no linking group between the phosphorus and fluorocarbon group, and (iii) combinations of (i) and (ii).

2. A recording medium according to claim 1 wherein said lubricant further comprises a solvent.

3. A recording medium comprising a lubricant and optionally a solvent wherein
said recording medium is magnetic medium, magneto-optical medium, or optical medium;
said lubricant comprises at least one phosphorus-containing compound having a formula represented by any one of Formula I to Formula XVII shown below:

(Formula I) $[Rf-Y-]_{(2-x)}-P(E)-[O_bC_6R_5][OM]_x$;
(Formula II) $[Rf''-Y-]_{(2-x)}-P(E)-[O_bC_6R_5][OM]_x$;
(Formula III) $[MO]_x[O_bC_6R_5]_{(2-x)}-P(E)-Y-Rf''-Y-P(E)-[O_bC_6R_5]_{(2-x)}[OM]_x$;
(Formula IV) $[Rf-]_{(2-x)}-P(E)-[O_bC_6R_5][OM]_x$;
(Formula V) $[Rf'-]_{(2-x)}-P(E)-[O_bC_6R_5][OM]_x$;
(Formula VI) $[MO]_x[O_bC_6R_5]_{(2-x)}-P(E)-Rf''-P(E)-[O_bC_6R_5]_{(2-x)}[OM]_x$;
(Formula VII) $[Rf-Y-]_{(3-y)}-P(E)_a-[OC_6R_5]_y$;
(Formula VIII) $[C_6R_5O]_2-P(E)_a-Y-Rf''-Y-P(E)_a-[OC_6R_5]_2$;
(Formula IX) $[Rf]_{(3-y)}-P(E)_a-[O_bC_6R_5]_y$;
(Formula X) $[Rf']_{(3-y)}-P(E)_a-[O_bC_6R_5]_y$;
(Formula XI) $[C_6R_5O]_2-P(E)_a-Rf''-P(E)_a-[O_bC_6R_5]_2$;
(Formula XII) $[Rf-Y-]_{(3-x)}-P(E)-[OM]_x$;
(Formula XIII) $[Rf''-Y]_{(3-x)}-P(E)-[OM]_x$;
(Formula XIV) $[Rf-Y]_{(2-x)}-[MO]_x-P(E)-Y-Rf''-Y-P(E)-[OM]_x-[Y-Rf-]_{(2-x)}$;
(Formula XV) $[Rf-]_{(3-x)}-P(E)-[OM]_x$;
(Formula XVI) $[Rf'-]_{(3-x)}-P(E)-[OM]_x$; and
(Formula XVII) $[Rf-]_{(2-x)}-[MO]_x-P(E)-Rf''-P(E)-[OM]_x-[-Rf-]_{(2-x)}$;

Rf is a polyether chain having a molecular weight from 400 to 15,000 and comprising repeating units selected from the group consisting of
J—O—$(CF(CF_3)CF_3O)_c$—$(CFXO)_d$—CFZ,
J$^1$—O—$(CF_2CF_2O)_e$—$(CF_2O)_f$—CFZ$^1$,
J$^2$—O—$(CF(CF_3)CF_2O)_j$—CF(CF$_3$), J$^3$—O—$(CQZ^2-CF_2CF_2-O)_k$—CQZ$^2$—CF$_2$,
J$^4$—O—$(CF_2CF_2O)_l$—CF$_2$, and
J$^5$—$(CF(CF_3)CF_2O)_g$—$(CF_2CF_2O)_h$—$(CFX-O)_i$—CFZ—;

J is CF$_3$, C$_2$F$_5$, C$_3$F$_7$, CF$_2$Cl, or C$_2$F$_4$Cl;
X is —F or —CF$_3$;
Z is —F, —Cl or —CF$_3$;
c and d are numbers such that the c/d ratio ranges from 0.01 to 0.5;
—J$^1$ is CF$_3$, C$_2$F$_5$, CF$_2$Cl, or C$_2$F$_4$Cl, or C$_3$F$_6$Cl;
Z$^1$ is —F or —Cl;
e and f are numbers such that the e/f ratio ranges from 0.5 to 2;

$J^2$ is $C_2F_5$ or $C_3F_7$;

j is a number such that the molecular weight Rf ranges from 400 to 15,000;

$J^3$ is $CF_3$, $C_2F_5$, or $C_3F_7$;

Q and $Z^2$, equal or different, are each F, Cl, or H;

k is a number such that the molecular weight of Rf ranges from 400 to 15,000;

$J^4$ is $CF_3$ or $C_2F_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is $(CH_2)_zO(CH_2CH_2O)_{z'}$ or $C_6R_4$; provided, in Formula VII, Y is $C_6R_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is $Z^2-(CF_2)_m$;

$Z^2$ is H, F, or Cl;

m has a value from 2 to 20;

Rf" is a perfluoropolyether chain selected from the group consisting of $(CF_2CF_2O)_n-(CF_2O)_o-CF_2$, $(C_3F_6O)_p-(CF_2CF_2O)_q-(CFXO)_r-CF_2$, $((CQZ^2)CF_2CF_2O)_s-CF_2-CF_2$, and $(CF_2O)-(CF_2CF_2O)_t-CF_2$;

the units with formulae $CF_2CF_2O$ and $CF_2O$ are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

4. A recording medium according to claim 2 wherein said lubricant comprises said phosphorus-containing compound having a formula represented by any one of Formula I to Formula XVII shown below:

(Formula I) $[Rf-Y-]_{(2-x)}-P(E)-[O_bC_6R_5][OM]_x$;

(Formula II) $[Rf'-Y-]_{(2-x)}-P(E)-[O_bC_6R_5][OM]_x$;

(Formula III) $[MO]_x[O_bC_6R_5]_{(2-x)}-P(E)-Y-Rf"-Y-P(E)-[O_bC_6R_5]_{(2-x)}[OM]_x$;

(Formula IV) $[Rf-]_{(2-x)}-P(E)-[O_bC_6R_5][OM]_x$;

(Formula V) $[Rf'-]_{(2-x)}-P(E)-[O_bC_6R_5][OM]_x$;

(Formula VI) $[MO]_x[O_bC_6R_5]_{(2-x)}-P(E)-Rf"-P(E)-[O_bC_6R_5]_{(2-x)}[OM]_x$;

(Formula VII) $[Rf-Y-]_{(3-y)}-P(E)_a-[OC_6R_5]_y$;

(Formula VIII) $[C_6R_5O]_2-P(E)_a-Y-Rf"-Y-P(E)_a-[OC_6R_5]_2$;

(Formula IX) $[Rf]_{(3-y)}-P(E)_a-[O_bC_6R_5]_y$;

(Formula X) $[Rf']_{(3-y)}-P(E)_a-[O_bC_6R_5]_y$;

(Formula XI) $[C_6R_5O]_2-P(E)_a-Rf"-P(E)_a-[O_bC_6R_5]_2$;

(Formula XII) $[Rf-Y-]_{(3-x)}-P(E)-[OM]_x$;

(Formula XIII) $[Rf'-Y]_{(3-x)}-P(E)-[OM]_x$;

(Formula XIV) $[Rf-Y]_{(2-x)}-[MO]_x-P(E)-Y-Rf"-Y-P(E)-[OM]_x-[Y-Rf-]_{(2-x)}$;

(Formula XV) $[Rf-]_{(3-x)}-P(E)-[OM]_x$;

(Formula XVI) $[Rf'-]_{(3-x)}-P(E)-[OM]_x$; and (Formula XVII) $[Rf-]_{(2-x)}-[MO]_x-P(E)-Rf"-P(E)-[OM]_x-[-Rf-]_{(2-x)}$;

Rf is a polyether chain having a molecular weight from 400 to 15,000 and comprising repeating units selected from the group consisting of $J-O-(CF(CF_3)CF_3O)_c-(CFXO)_d-CFZ$, $J^1-O-(CF_2CF_2O)_e-(CF_2O)_f-CFZ^1$, $J^2-O-(CF(CF_3)CF_2O)_j-CF(CF_3)$, $J^3-O-(CQZ^2-CF_2CF_2-O)_k-CQZ^2-CF_2$, $J^4-O-(CF_2CF_2O)_l-CF_2$, and $J^5-(CF(CF_3)CF_2O)_g-(CF_2CF_2O)_h-(CFX-O)_i-CFZ-$;

J is $CF_3$, $C_2F_5$, $C_3F_7$, $CF_2Cl$, or $C_2F_4Cl$;

X is $-F$ or $-CF_3$;

Z is $-F$, $-Cl$ or $-CF_3$;

c and d are numbers such that the c/d ratio ranges from 0.01 to 0.5;

$J^1$ is $CF_3$, $C_2F_5$, $CF_2Cl$, or $C_2F_4Cl$;

$Z^1$ is $-F$ or $-Cl$;

e and f are numbers such that the e/f ratio ranges from 0.5 to 2;

$J^2$ is $C_2F_5$ or $C_3F_7$;

j is a number such that the molecular weight Rf ranges from 400 to 15,000;

$J^3$ is $CF_3$, $C_2F_5$, or $C_3F_7$;

Q and $Z^2$, equal or different, are each F, Cl, or H;

k is a number such that the molecular weight of Rf ranges from 400 to 15,000;

$J^4$ is $CF_3$ or $C_2F_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is $(CH_2)_zO(CH_2CH_2O)_{z'}$ or $C_6R_4$; provided, in Formula VII, Y is $C_6R_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is $Z^2-(CF_2)_m$;

$Z^2$ is H, F, or Cl;

m has a value from 2 to 20;

Rf" is a perfluoropolyether chain selected from the group consisting of $(CF_2CF_2O)_n-(CF_2O)_o-CF_2$, $(C_3F_6O)_p-(CF_2CF_2O)_q-(CFXO)_r-CF_2$, $((CQZ^2)CF_2CF_2O)_s-CF_2-CF_2$, and $(CF_2O)-(CF_2CF_2O)_t-CF_2$;

the units with formulae $CF_2CF_2O$ and $CF_2O$ are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

5. A recording medium according to claim 1 having coated with therewith said a lubricant.

6. A recording medium according to claim 5 wherein said lubricant comprises at least one phosphorus compound represented by any one of Formula I to Formula XVII shown below:

(Formula I) $[Rf—Y—]_{(2-x)}—P(E)—[O_bC_6R_5][OM]_x$;

(Formula II) $[Rf'—Y—]_{(2-x)}—P(E)—[O_bC_6R_5][OM]_x$;

(Formula III) $[MO]_x[O_bC_6R_5]_{(2-x)}—P(E)—Y—Rf"—Y—P(E)—[O_bC_6R_5]_{(2-x)}[OM]_x$;

(Formula IV) $[Rf—]_{(2-x)}—P(E)—[O_bC_6R_5][OM]_x$;

(Formula V) $[Rf'—]_{(2-x)}—P(E)—[O_bC_6R_5][OM]_x$;

(Formula VI) $[MO]_x[O_bC_6R_5]_{(2-x)}—P(E)—Rf"—P(E)—[O_bC_6R_5]_{(2-x)}[OM]_x$;

(Formula VII) $[Rf—Y—]_{(3-y)}—P(E)_a—[OC_6R_5]_y$;

(Formula VIII) $[C_6R_5O]_2—P(E)_a—Y—Rf"—Y—P(E)_a—[OC_6R_5]_2$;

(Formula IX) $[Rf]_{(3-y)}—P(E)_a—[O_bC_6R_5]_y$;

(Formula X) $[Rf']_{(3-y)}—P(E)_a—[O_bC_6R_5]_y$;

(Formula XI) $[C_6R_5O]_2—P(E)_a—Rf"—P(E)_a—[O_bC_6R_5]_2$;

(Formula XII) $[Rf—Y—]_{(3-x)}—P(E)—[OM]_x$;

(Formula XIII) $[Rf'—Y]_{(3-x)}—P(E)—[OM]_x$;

(Formula XIV) $[Rf—Y]_{(2-x)}—[MO]_x—P(E)—Y—Rf"—Y—P(E)—[OM]_x—[Y—Rf—]_{(2-x)}$;

(Formula XV) $[Rf—]_{(3-x)}—P(E)—[OM]_x$;

(Formula XVI) $[Rf'—]_{(3-x)}—P(E)—[OM]_x$; and (Formula XVII) $[Rf—]_{(2-x)}—[MO]_x—P(E)—Rf"—P(E)—[OM]_x—[—Rf—]_{(2-x)}$;

Rf is a polyether chain having a molecular weight from 400 to 15,000 and comprising repeating units selected from the group consisting of
$J—O—(CF(CF_3)CF_2 3O)_c—(CFXO_d—CFZ$, $J^1—O—(CF_2CF_2O)_e—(CF_2O)_f—CFZ^1$,
$J^2—O—(CF(CF_3)CF_2O)_jCF(CF_3)$, $J^3—O—(CQZ^2—CF_2CF_2—O)_k—CQZ^2—CF_2$,
$J^4—O—(CF_2CF_2O)_l—CF_2$, and
$J^5—(CF(CF_3)CF_2O)_g—(CF_2CF_2O)_h—(CFX—O)_i—CFZ—$;

J is $CF_3$, $C_2F_5$, $C_3F_7$, $CF_2Cl$, or $C_2F_4Cl$;

X is —F or —$CF_3$;

Z is —F, —Cl or —$CF_3$;

c and d are numbers such that the c/d ratio ranges from 0.01 to 0.5;

$J^1$ is $CF_3$, $C_2F_5$, $CF_2Cl$, or $C_2F_4Cl$;

$Z^1$ is —F or —Cl;

e and f are numbers such that the e/f ratio ranges from 0.5 to 2;

$J^2$ is $C_2F_5$ or $C_3F_7$;

j is a number such that the molecular weight Rf ranges from 400 to 15,000;

$J^3$ is $CF_3$, $C_2F_5$, or $C_3F_7$;

Q and $Z^2$, equal or different, are each F, Cl, or H;

k is a number such that the molecular weight of Rf ranges from 400 to 15,000;

$J^4$ is $CF_3$ or $C_2F_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is $(CH_2)_zO(CH_2CH_2O)_{z'}$ or $C_6R_4$; provided, in Formula VII, Y is $C_6R_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is $Z^2—(CF_2)_m$;

$Z^2$ is H, F, or Cl;

m has a value from 2 to 20;

Rf" is a perfluoropolyether chain selected from the group consisting of
$(CF_2CF_2O)_n—(CF_2O)_o—CF_2$, $(C_3F_6O)_p—(CF_2CF_2O)_q—(CFXO)_r—CF_2$, $((CQZ^2)$
$CF_2CF_2O)_s—CF_2—CF_2$, and $(CF_2O)—(CF_2CF_2O)_t—CF_2$;

the units with formulae $CF_2CF_2O$ and $CF_2O$ are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

7. A recording medium according to claim 6 wherein said lubricant further comprises a solvent.

8. A recording medium according to claim 1 wherein said phosphorus-containing compound has a formula represented by any one of Formula I to XVII represented by any one of Formula I to Formula XVII shown below:

(Formula I) $[Rf—Y—]_{(2-x)}—P(E)—[O_bC_6R_5][OM]_x$;

(Formula II) $[Rf'—Y—]_{(2-x)}—P(E)—[O_bC_6R_5][OM]_x$;

(Formula III) $[MO]_x[O_bC_6R_5]_{(2-x)}—P(E)—Y—Rf"—Y—P(E)—[O_bC_6R_5]_{(2-x)}[OM]_x$;

(Formula IV) $[Rf—]_{(2-x)}—P(E)—[O_bC_6R_5][OM]_x$;

(Formula V) $[Rf'—]_{(2-x)}—P(E)—[O_bC_6R_5][OM]_x$;

(Formula VI) $[MO]_x[O_bC_6R_5]_{(2-x)}—P(E)—Rf"—P(E)—[O_bC_6R_5]_{(2-x)}[OM]_x$;

(Formula VII) $[Rf—Y—]_{(3-y)}—P(E)_a—[OC_6R_5]_y$;

(Formula VIII) $[C_6R_5O]_2—P(E)_a—Y—Rf"—Y—P(E)_a—[OC_6R_5]_2$;

(Formula IX) $[Rf]_{(3-y)}—P(E)_a—[O_bC_6R_5]_y$;

(Formula X) $[Rf']_{(3-y)}—P(E)_a—[O_bC_6R_5]_y$;

(Formula XI) $[C_6R_5O]_2—P(E)_a—Rf"—P(E)_a—[O_bC_6R_5]_2$;

(Formula XII) $[Rf—Y—]_{(3-x)}—P(E)—[OM]_x$;

(Formula XIII) $[Rf'—Y]_{(3-x)}—P(E)—[OM]_x$;

(Formula XIV) $[Rf—Y]_{(2-x)}—[MO]_x—P(E)—Y—Rf"—Y—P(E)—[OM]_x—[Y—Rf—]_{(2-x)}$;

(Formula XV) $[Rf—]_{(3-x)}—P(E)—[OM]_x$;

(Formula XVI) $[Rf'—]_{(3-x)}—P(E)—[OM]_x$; and (Formula XVII) $[Rf—]_{(2-x)}—[MO]_x—P(E)—Rf"—P(E)—[OM]_x—[—Rf—]_{(2-x)}$;

Rf is a polyether chain having a molecular weight from 400 to 15,000 and comprising repeating units selected from the group consisting of J—O—(CF(CF$_3$)CF$_2$$_3$O)$_c$—(CFXO$_d$—CFZ, J$^1$—O—(CF$_2$CF$_2$O)$_e$—(CF$_2$O)$_f$—CFZ$^1$,
J$^2$—O—(CF(CF$_3$)CF$_2$O)$_j$—CF(CF$_3$), J$^3$—O—(CQZ$^2$—CF$_2$CF$_2$—O)$_k$—CQZ$^2$—CF$_2$,
J$^4$—O—(CF$_2$CF$_2$O)$_l$—CF$_2$, and
J$^5$—(CF(CF$_3$)CF$_2$O)$_g$—(CF$_2$CF$_2$O)$_h$—(CFX—O)$_i$—CFZ—;

J is CF$_3$, C$_2$F$_5$, C$_3$F$_7$, CF$_2$Cl, C$_2$F$_4$Cl, or —

X is —F or —CF$_3$;

Z is —F, —Cl or —CF$_3$;

c and d are numbers such that the c/d ratio ranges from 0.01 to 0.5;

J$^1$ is CF$_3$, C$_2$F$_5$, CF$_2$Cl, or C$_2$F$_4$Cl;

Z$^1$ is —F or —Cl;

e and f are numbers such that the e/f ratio ranges from 0.5 to 2;

J$^2$ is C$_2$F$_5$ or C$_3$F$_7$;

j is a number such that the molecular weight Rf ranges from 400 to 15,000;

J$^3$ is CF$_3$, C$_2$F$_5$, or C$_3$F$_7$;

Q and Z$^2$, equal or different, are each F, Cl, or H;

k is a number such that the molecular weight of Rf ranges from 400 to 15,000;

J$^4$ is CF$_3$ or C$_2$F$_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is (CH$_2$)$_z$O(CH$_2$CH$_2$O)$_{z'}$ or C$_6$R$_4$; provided, in Formula VII, Y is C$_6$R$_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is Z$^2$—(CF$_2$)$_m$;

Z$^2$ is H, F, or Cl;

m has a value from 2 to 20;

Rf" is a perfluoropolyether chain selected from the group consisting of
(CF$_2$CF$_2$O)$_n$—(CF$_2$O)$_o$—CF$_2$, (C$_3$F$_6$O)$_p$—(CF$_2$CF$_2$O)$_q$—(CFXO)$_r$—CF$_2$, ((CQZ$^2$)CF$_2$CF$_2$O)$_s$—CF$_2$—CF$_2$, and (CF$_2$O)—(CF$_2$CF$_2$O)$_t$—CF$_2$;

the units with formulae CF$_2$CF$_2$O and CF$_2$O are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

9. A process comprising contacting a recording medium with a lubricant wherein said recording medium is magnetic medium, magneto-optical medium, or optical medium and said lubricant wherein said lubricant comprises a phosphorus-containing fluorocarbon compound selected from the group consisting of compound A, compound B, compound C, and combinations of two or more thereof;

said compound A is a perfluoropolyether- or perfluoroalkyl-containing and phosphorus-containing compound selected from the group consisting of partially esterified aryl phosphates, partially esterified aryl phosphonates, and salts thereof, containing either (i) a mono-alkylene oxide or poly-alkylene oxide or phenylene oxide linking group between the phosphorus and a fluorocarbon group, (ii) no linking group between the phosphorus and fluorocarbon group, or (iii) combinations of (i) and (ii);

said compound B is an asymmetrical perfluoropolyether- or perfluoroalkyl-containing and phosphorus-containing compound selected from the group consisting of (i) aryl phosphites or phosphates containing a phenylene oxide linking group between the phosphorus and a perfluoroether group, (ii) aryl phosphines, aryl phosphinites, aryl phosphonites, aryl phosphine oxides, aryl phosphinates or aryl phosphonates with no linking group between the phosphorus and a fluorocarbon group, and (iii) combinations of (i) and (ii); and said compound C is a perfluoropolyether- or perfluoroalkyl-containing and phosphorus-containing compound selected from the group consisting of partially esterified phosphates, partially esterified phosphonates, and salts thereof, containing either (i) phenylene oxide linking group between the phosphorus and a fluorocarbon group, (ii) no linking group between the phosphorus and fluorocarbon group, and (iii) combinations of (i) and (ii).

10. A process according to claim 9 wherein said process is carried out by dip coating, spin coating, spraying coating, or vapor deposition.

11. A process according to claim 9 wherein said lubricant comprises a phosphorus compound represented by any one of Formula I to Formula XVII shown below:

(Formula I) [Rf—Y—]$_{(2-x)}$—P(E)—[O$_b$C$_6$R$_5$][OM]$_x$;

(Formula II) [Rf'—Y—]$_{(2-x)}$—P(E)—[O$_b$C$_6$R$_5$][OM]$_x$;

(Formula III) [MO]$_x$[O$_b$C$_6$R$_5$]$_{(2-x)}$—P(E)—Y—Rf"—Y—P(E)—[O$_b$C$_6$R$_5$]$_{(2-x)}$[OM]$_x$;

(Formula IV) [Rf—]$_{(2-x)}$—P(E)—[O$_b$C$_6$R$_5$][OM]$_x$;

(Formula V) [Rf'—]$_{(2-x)}$—P(E)—[O$_b$C$_6$R$_5$][OM]$_x$;

(Formula VI) [MO]$_x$[O$_b$C$_6$R$_5$]$_{(2-x)}$—P(E)—Rf"—P(E)—[O$_b$C$_6$R$_5$]$_{(2-x)}$[OM]$_x$;

(Formula VII) [Rf—Y—]$_{(3-y)}$—P(E)$_a$—[OC$_6$R$_5$]$_y$;

(Formula VIII) [C$_6$R$_5$O]$_2$—P(E)$_a$—Y—Rf"—Y—P(E)$_a$—[OC$_6$R$_5$]$_2$;

(Formula IX) [Rf]$_{(3-y)}$—P(E)$_a$—[O$_b$C$_6$R$_5$]$_y$;

(Formula X) [Rf']$_{(3-y)}$—P(E)$_a$—[O$_b$C$_6$R$_5$]$_y$;

(Formula XI) [C$_6$R$_5$O]$_2$—P(E)$_a$—Rf"—P(E)$_a$—[O$_b$C$_6$R$_5$]$_2$;

(Formula XII) [Rf—Y—]$_{(3-x)}$—P(E)—[OM]$_x$;

(Formula XIII) [Rf'—Y]$_{(3-x)}$—P(E)—[OM]$_x$;

(Formula XIV) [Rf—Y]$_{(2-x)}$—[MO]$_x$—P(E)—Y—Rf"—Y—P(E)—[OM]$_x$—[Y—Rf—]$_{(2-x)}$;

(Formula XV) [Rf—]$_{(3-x)}$—P(E)—[OM]$_x$;

(Formula XVI) [Rf'—]$_{(3-x)}$—P(E)—[OM]$_x$; and (Formula XVII) [Rf—]$_{(2-x)}$—[MO]$_x$—P(E)—Rf"—P(E)—[OM]$_x$—[—Rf—]$_{(2-x)}$;

Rf is a polyether chain having a molecular weight from 400 to 15,000 and comprising repeating units selected from the group consisting of J—O—(CF(CF$_3$)CF$_3$O)$_c$—(CFXO$_d$—CFZ, J$^1$—O—(CF$_2$CF$_2$O)$_e$—(CF$_2$O)$_f$—CFZ$^1$,
J$^2$—O—(CF(CF$_3$)CF$_2$O)$_j$—CF(CF$_3$), J$^3$—O—(CQZ$^2$—CF$_2$CF$_2$—O)$_k$—CQZ$^2$—CF$_2$,
J$^4$—O—(CF$_2$CF$_2$O)$_l$—CF$_2$, and
J$^5$—(CF(CF$_3$)CF$_2$O)$_g$—(CF$_2$CF$_2$O)$_h$—(CFX—O)$_i$—CFZ—;

J is CF$_3$, C$_2$F$_5$, C$_3$F$_7$, CF$_2$Cl, C$_2$F$_4$Cl, or C$_3$F$_6$Cl;

X is —F or —CF$_3$;

Z is —F, —Cl or —CF$_3$;

c and d are numbers such that the c/d ratio ranges from 0.01 to 0.5;

J$^1$ is CF$_3$, C$_2$F$_5$, CF$_2$Cl, or C$_2$F$_4$Cl;

Z$^1$ is —F or —Cl;

e and f are numbers such that the e/f ratio ranges from 0.5 to 2;

J$^2$ is C$_2$F$_5$ or C$_3$F$_7$;

j is a number such that the molecular weight Rf ranges from 400 to 15,000;

J$^3$ is CF$_3$, C$_2$F$_5$, or C$_3$F$_7$;

Q and Z$^2$, equal or different, are each F, Cl, or H;

k is a number such that the molecular weight of Rf ranges from 400 to 15,000;

J$^4$ is CF$_3$ or C$_2$F$_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is (CH$_2$)$_z$O(CH$_2$CH$_2$O)$_{z'}$ or C$_6$R$_4$; provided, in Formula VII, Y is C$_6$R$_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is Z$^2$—(CF$_2$)$_m$;

Z$^2$ is H, F, or Cl;

m has a value from 2 to 20;

Rf" is a perfluoropolyether chain selected from the group consisting of
(CF$_2$CF$_2$O)$_n$—(CF$_2$O)$_o$—CF$_2$, (C$_3$F$_6$O)$_p$—(CF$_2$CF$_2$O)$_q$—(CFXO)$_r$—CF$_2$, ((CQZ$^2$)CF$_2$CF$_2$O)$_s$—CF$_2$—CF$_2$, and (CF$_2$O)—(CF$_2$CF$_2$O)$_t$—CF$_2$;

the units with formulae CF$_2$CF$_2$O and CF$_2$O are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

12. A process according to claim 9 wherein said lubricant further comprises a solvent.

13. A process according to claim 10 wherein said lubricant further comprises a solvent.

14. A process according to claim 10 wherein said lubricant comprises a phosphorus compound represented by any one of Formula I to Formula XVII shown below:

(Formula I) [Rf—Y—]$_{(2-x)}$—P(E)—[O$_b$C$_6$R$_5$][OM]$_x$;

(Formula II) [Rf'—Y—]$_{(2-x)}$—P(E)—[O$_b$C$_6$R$_5$][OM]$_x$;

(Formula III) [MO]$_x$[O$_b$C$_6$R$_5$]$_{(2-x)}$—P(E)—Y—Rf"—Y—P(E)—[O$_b$C$_6$R$_5$]$_{(2-x)}$[OM]$_x$;

(Formula IV) [Rf—]$_{(2-x)}$—P(E)—[O$_b$C$_6$R$_5$][OM]$_x$;

(Formula V) [Rf'—]$_{(2-x)}$—P(E)—[O$_b$C$_6$R$_5$][OM]$_x$;

(Formula VI) [MO]$_x$[O$_b$C$_6$R$_5$]$_{(2-x)}$—P(E)—Rf"—P(E)—[O$_b$C$_6$R$_5$]$_{(2-x)}$[OM]$_x$;

(Formula VII) [Rf—Y—]$_{(3-y)}$—P(E)$_a$—[OC$_6$R$_5$]$_y$;

(Formula VIII) [C$_6$R$_5$O]$_2$—P(E)$_a$—Y—Rf"—Y—P(E)$_a$—[OC$_6$R$_5$]$_2$;

(Formula IX) [Rf]$_{(3-y)}$—P(E)$_a$—[O$_b$C$_6$R$_5$]$_y$;

(Formula X) [Rf']$_{(3-y)}$—P(E)$_a$—[O$_b$C$_6$R$_5$]$_y$;

(Formula XI) [C$_6$R$_5$O]$_2$—P(E)$_a$—Rf"—P(E)$_a$—[O$_b$C$_6$R$_5$]$_2$;

(Formula XII) [Rf—Y—]$_{(3-x)}$—P(E)—[OM]$_x$;

(Formula XIII) [Rf'—Y]$_{(3-x)}$—P(E)—[OM]$_x$;

(Formula XIV) [Rf—Y—]$_{(2-x)}$—[MO]$_x$—P(E)—Y—Rf"—Y—P(E)—[OM]$_x$—[Y—Rf—]$_{(2-x)}$;

(Formula XV) [Rf—]$_{(3-x)}$—P(E)—[OM]$_x$;

(Formula XVI) [Rf'—]$_{(3-x)}$—P(E)—[OM]$_x$; and (Formula XVII) [Rf—]$_{(2-x)}$—[MO]$_x$—P(E)—Rf"—P(E)—[OM]$_x$—[—Rf—]$_{(2-x)}$;

Rf is a polyether chain having a molecular weight from 400 to 15,000 and comprising repeating units selected from the group consisting of
J—O—(CF(CF$_3$)CF$_3$O)$_c$—(CFXO$_d$—CFZ, J$^1$—O—(CF$_2$CF$_2$O)$_e$—(CF$_2$O)$_f$—CFZ$^1$,
J$^2$—O—(CF(CF$_3$)CF$_2$O)$_j$CF—(CF$_3$), J$^3$—O—(CQZ$^2$—CF$_2$CF$_2$—O)$_k$—CQZ$^2$—CF$_2$,
J$^4$—O—(CF$_2$CF$_2$O)$_l$—CF$_2$, and
J$^5$—(CF(CF$_3$)CF$_2$O)$_g$—(CF$_2$CF$_2$O)$_h$—(CFX—O)$_i$—CFZ—;

J is CF$_3$, C$_2$F$_5$, C$_3$F$_7$, CF$_2$Cl, C$_2$F$_4$Cl, or C$_3$F$_6$Cl;

X is —F or —CF$_3$;

Z is —F, —Cl or —CF$_3$;

c and d are numbers such that the c/d ratio ranges from 0.01 to 0.5;

J$^1$ is CF$_3$, C$_2$F$_5$, CF$_2$Cl, or C$_2$F$_4$Cl;

Z$^1$ is —F or —Cl;

e and f are numbers such that the e/f ratio ranges from 0.5 to 2;

J$^2$ is C$_2$F$_5$ or C$_3$F$_7$;

j is a number such that the molecular weight Rf ranges from 400 to 15,000;

J$^3$ is CF$_3$, C$_2$F$_5$, or C$_3$F$_7$;

Q and Z$^2$, equal or different, are each F, Cl, or H;

k is a number such that the molecular weight of Rf ranges from 400 to 15,000;

J$^4$ is CF$_3$ or C$_2$F$_5$;

l is a number such that the molecular weight of Rf ranges from 400 to 5,000;

g, h and i are numbers such that (g+h) ranges from 1 to 50, the i/(g+h) ratio ranges from 0.1 to 0.05;

Y is (CH$_2$)$_z$O(CH$_2$CH$_2$O)$_{z'}$ or C$_6$R$_4$; provided, in Formula VII, Y is C$_6$R$_4$;

z is 1 to 4;

z' is 0, 1, or 2;

x is 0.05 to 1;

E is oxygen or sulfur;

b is 0 or 1;

R is independently hydrogen, halogen, alkyl, aryl, nitro, cyano, alkoxy, amino, sulfonyl, carboxyl, or phenoxy;

M is hydrogen, alkali metal, alkaline earth metal, or ammonium;

Rf' is $Z^2-(CF_2)_m$;

$Z^2$ is H, F, or Cl;

m has a value from 2 to 20;

Rf" is a perfluoropolyether chain selected from the group consisting of
$(CF_2CF_2O)_n-(CF_2O)_o-CF_2$, $(C_3F_6O)_p-(CF_2CF_2O)_q-(CFXO)_r-CF_2$, $((CQZ^2)CF_2CF_2O)_s-CF_2-CF_2$, and $(CF_2O)-(CF_2CF_2O)_t-CF_2$;

the units with formulae $CF_2CF_2O$ and $CF_2O$ are randomly distributed along the chain;

the ratio of n/o is in the range of from 0.3 to 5;

p, q and r are numbers such that (p+q) ranges from 1 to 50, the r/(p+q) ratio ranges from 0.1 to 0.05;

s and t are each a number such that the molecular weight of Rf" ranges from 400 to 15,000;

y is 0.05 to 2; and a is 0 or 1.

15. A process according to claim 14 wherein said lubricant further comprises a solvent.

16. A recording medium according to claim 6 wherein said lubricant further comprises a solvent.

17. A recording medium according to claim 3 wherein said lubricant further comprises a solvent.

18. A recording medium according to claim 3 wherein said phosphorus-containing fluorocarbon compound is $F(CF(CF_3)CF_2O)_nCF(CF_3)CH_2OP(O)[OH]C_6H_5$, $F(CF(CF_3)CF_2O)_nCF(CF_3)CH_2OP(O)[OH]OC_6H_5$, $F(CF_2)_mCH_2CH_2OP(O)[OH]C_6H_5$, $F(CF_2)_mCH_2CH_2OP(O)[OH]OC_6R_5$, $[HO](C_6H_5)P(O)OCH_2(CF_2CF_2O)_n(CF_2O)_oCF_2CH_2OP(O)(C_6H_5)[OH]$, $[HO](OC_6H_5)P(O)OCH_2(CF_2CF_2O)_n(CF_2O)_oCF_2CH_2OP(O)(OC_6H_5)[OH]$, $F(CF(CF_3)CF_2O)_nCF(CF_3)P(O)[OH]C_6H_5$, $F(CF(CF_3)CF_2O)_nCF(CF_3)P(O)[OH]OC_6H_5$, $F(CF_2)_mP(O)[OH]C_6H_5$, $F(CF_2)_mP(O)[OH]OC_6H_5$, $[HO](C_6H_5)P(O)(CF_2CF_2O)_n(CF_2O)_oCF_2P(O)(C_6H_5)[OH]$, $[HO](OC_6H_5)P(O)(CF_2CF_2O)_n(CF_2O)_oCF_2P(O)(OC_6H_5)[OH]$, $[F(CF(CF_3)CF_2O)_nCF(CF_3)CH_2O]P(OC_6H_5)_2$, $[F(CF(CF_3)CF_2O)_nCF(CF_3)CH_2O]_2P(O)(OC_6H_5)$, $(C_6H_5O)_2P(CF_2CF_2O)_n(CF_2O)_oCF_2P(OC_6H_5)_2$, $(OC_6H_5)P(O)(CF_2CF_2O)_n(CF_2O)_oCF_2P(O)(OC_6H_5)_2$, $F(CF(CF_3)CF_2O)_nCF(CF_3)(C_6H_5)_2$, $F(CF(CF_3)CF_2O)_nCF(CF_3)_2P(OC_6H_5)$, $[F(CF(CF_3)CF_2O)_nCF(CF_3)]P(O)(C_6H_5)_2$, $[F(CF(CF_3)CF_2O)_nCF(CF_3)]_2P(O)(OC_6H_5)$, $F(CF_2)_mP(C_6H_5)_2$, $[F(CF_2)_m]_2P(OC_6H_5)$, $F(CF_2)_mP(O)(OC_6H_5)_2$ $[F(CF_2)_m]P(O)(OC_6H_5)_2$, $(C_6H_5)_2P(CF_2CF_2O)_n(CF_2O)_oCF_2P(C_6H_5)_2$, $(OC_6H_5)P(CF_2CF_2O)_n(CF_2O)_oCF_2P(OC_6H_5)_2$, $(C_6H_5)_2P(O)(CF_2CF_2O)_n(CF_2O)_oCF_2P(O)(C_6H_5)_2$, $(OC_6H_5)_2P(O)(CF_2CF_2O)_n(CF_2O)_oCF_2P(O)(OC_6H_5)_2$, $F(CF(CF_3)CF_2O)_nCF(CF_3)CH_2OP(O)(OH)_2$, $[F(CF(CF_3)CF_2O)_nCF(CF_3) CH_2O]_2P(O)(OH)_2$, $F(CF_2)_mCH_2CH_2OP(O)[OH]_2$, $[F(CF_2)_mCH_2CH_2]_2P(O)[OH]$, $[HO]_2P(O)OCH_2(CF_2CF_2O)_n(CF_2O)_oCF_2CH_2OP(O)(OH)_2$, $$\begin{array}{c} P(O)(OH)[OCH_2CF(CF_3)(OCF_2CF(CF3))_jF] \\ | \\ OCH_2(CF_2CF_2O)_n(CF_2O)_oCF_2CH_2OP(O)(OH) \\ | \\ [OCH_2CF(CF_3)(OCF_2CF(CF3))_jF] \end{array},$$

$F(CF(CF_3)CF_2O)_nCF(CF_3)P(O)(OH)_2$, $[F(CF(CF_3)CF_2O)_nCF(CF_3]_2P(O)(OH)_2$, $[F(CF_2)_m]_2P(O)[OH]_2$, $[F(CF_2)_m]_2P(O)[OH]$, $[HO]_2P(O)CF_2O(CF_2CF_2O)_n(CF_2O)_oCF_2P(O)(OH)_2$, or $$\begin{array}{c} (HO)P(O)[CF(CF_3)(OCF_2CF(CF3))_jF] \\ | \\ OCH_2(CF_2CF_2O)_n(CF_2O)_oCF_2CH_2OP(O)(OH) \\ | \\ [CF(CF_3)(OCF_2CF(CF3))_jF] \end{array}$$

where n is 4 to 10; where m is 4, 6 or 8; where (n+o)=8 and n/o=1 and j=4 to 10.

19. A recording medium according to claim 18 wherein said lubricant further comprises a solvent.

* * * * *